United States Patent [19]
Wilson

[11] 4,287,408
[45] Sep. 1, 1981

[54] COMBINATION ELECTRICALLY HEATED MATERIAL RECEPTACLE AND INSTRUMENT HEATER

[76] Inventor: Melvin Wilson, 16 Lanier Dr., Cumming, Ga. 30130

[21] Appl. No.: 128,509

[22] Filed: Mar. 10, 1980

[51] Int. Cl.³ .......................... H05B 1/00; H05B 3/68; F27B 14/06
[52] U.S. Cl. .................................... 219/475; 126/240; 165/96; 219/214; 219/242; 219/385; 219/421; 219/436; 219/521; 219/536; 228/56; 401/1; 433/32
[58] Field of Search ............... 219/221, 242, 214, 200, 219/201, 475, 476, 420–427, 385, 386, 433–438, 520, 521, 536, 472; 165/96; 433/32; 401/1–3; 228/56; 99/339; 126/236–241, 284, 413, 414

[56] References Cited
U.S. PATENT DOCUMENTS

| | | | |
|---|---|---|---|
| 1,264,174 | 4/1918 | Furber | 219/475 |
| 2,045,466 | 6/1936 | Hellbach | 219/385 |
| 2,268,686 | 1/1942 | Weekes | 219/521 |
| 2,769,387 | 11/1956 | Penick | 219/242 X |
| 3,095,605 | 7/1963 | Finelt | 219/426 X |
| 3,385,954 | 5/1968 | Rabinowitz et al. | 219/421 |

Primary Examiner—A. Bartis
Attorney, Agent, or Firm—Jones, Thomas & Askew

[57] ABSTRACT

A materials heating device includes rod-shaped electrical heating element which serves both to heat a thermoconductive receptacle containing the material to be heated as well as tools and instruments for working with the material. The heating element is mounted in spaced relationship to the receptacle by a thermoconductive bracket through which heat is conducted to the receptacle to heat the contents thereof. The end of the heating element protrudes from the bracket, whereby tools and instruments to be heated can be held in direct contact with the exposed end portion of the heating element until sufficient heat is transferred thereto. An adjustable heat dissipator can be provided on the receptacle to regulate the temperature of the receptacle.

4 Claims, 4 Drawing Figures

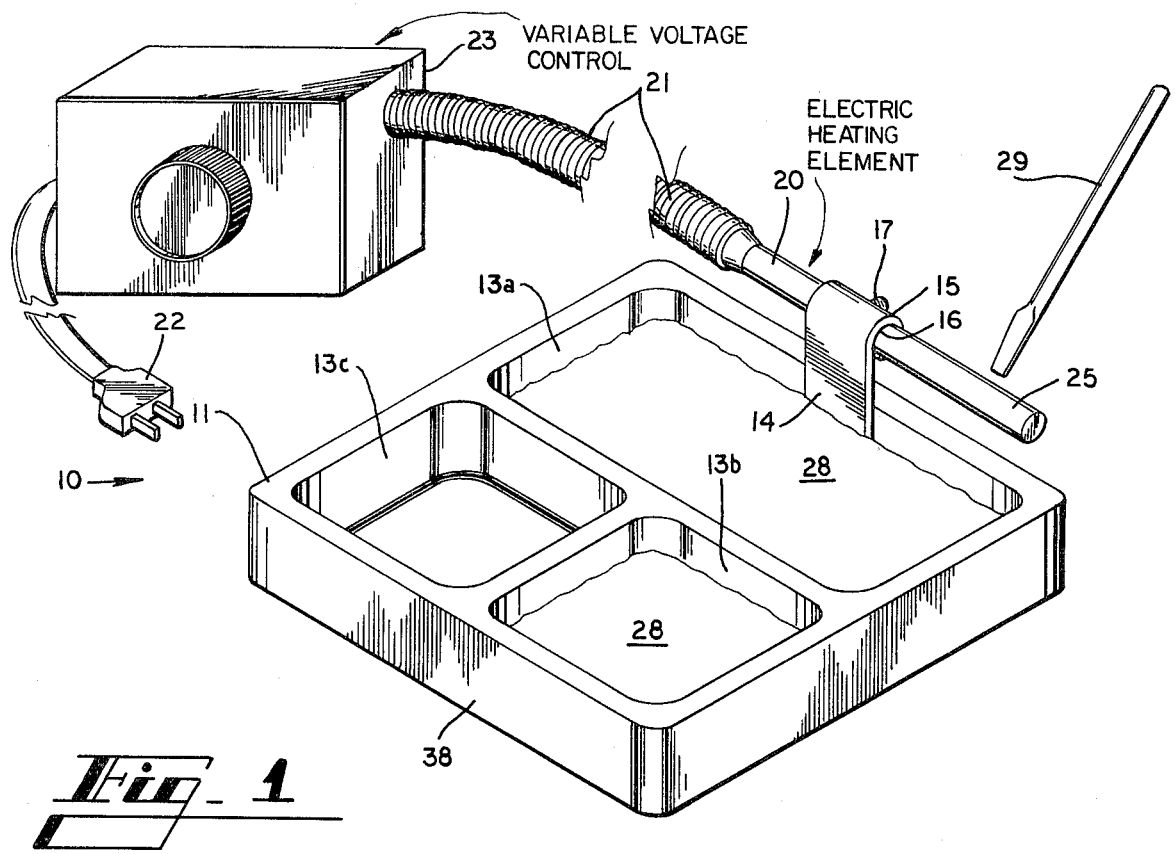
Fig. 1
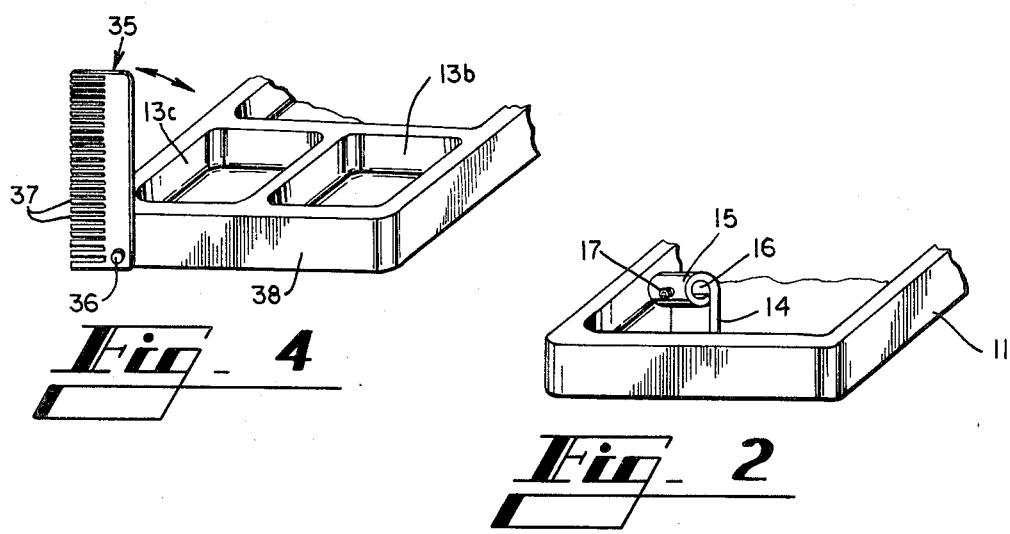
Fig. 4
Fig. 2
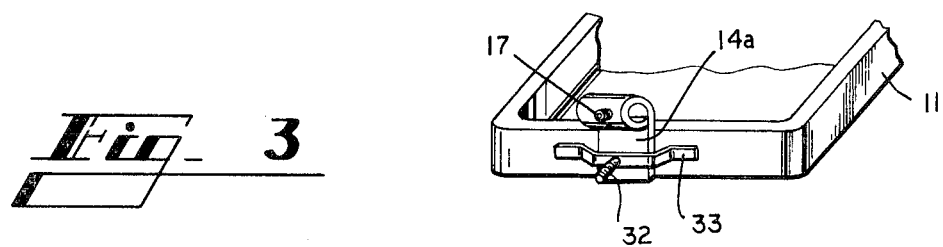
Fig. 3

COMBINATION ELECTRICALLY HEATED MATERIAL RECEPTACLE AND INSTRUMENT HEATER

BACKGROUND OF THE INVENTION

The present invention relates generally to devices used for heating molten material, such as wax, and for heating tools used to handle the molten material. More specifically the invention relates to the field of dental prosthetics and to a device for heating wax and tools used in making dental impressions.

Prior to the widespread use of electrically heated dishes or pots, the main source of heat for use by a dentist or dental technician in making wax pattern dental impressions was a Bunsen burner. Once the wax was melted and ready for use, the spoon, knife or other instrument used to work the wax was preheated in the Bunsen burner. The heated instrument was then dipped into a dish of unmelted wax, which melted and collected a small amount of wax on the tip of the instrument, and the instrument was then returned to the Bunsen burner for the wax to be reheated to a workable state.

Eventually, the electrically heated dish was employed to keep the wax in a molten state, thereby eliminating the time-consuming step of melting the wax with the instrument. But, since there existed no practical alternative method for heating the working instruments, the Bunsen burner was retained for the purpose of heating the instruments.

The existing arrangement of Bunsen burner and electrically heated dish creates a number of problems. One problem is the added expense of owning and operating two energy-using heating units, particularly where the heat of the open Bunsen flame adds to the air-conditioning load of the work space. There is further inconvenience in maintaining two heating units and in the fact that two units occupy too much space in the work room. Moreover, the open flame of a Bunsen burner creates hazardous working conditions.

SUMMARY OF THE INVENTION

Briefly described, the apparatus of the present invention comprises a heating unit which includes an electrical heating element which serves to heat both the wax pot and the wax-working instruments. The heating element is attached by a thermoconductive path to a wax heating dish also made of thermoconductive material. Heat is conducted from the heating element through the thermoconductive path to the heating dish sufficient to melt the wax and keep the wax in molten state. Furthermore, the heating element is held by the bracket with a portion of the element exposed so that the element can be contacted by the wax-working instruments. It is this exposed portion of the heating element which serves as the instrument heating device to heat the dentist's or technician's instruments and thus finally eliminate the need for a Bunsen burner or other supplemental heating unit. The instruments are heated by being brought directly into contact with the hot, exposed portion of the heating element and being held in contact until sufficient heat is transferred to the instrument.

The heating dish and instrument heating device of the present invention are conveniently integrally constructed as parts of the same heating unit and are served by the same heating element. The instruments are heated in close proximity to the wax and, therefore, there is only a short transfer distance.

It is therefore an object of the present invention to provide a heating unit which can both heat and hold a fluid in molten state and heat solid materials at a station in close proximity to the molten fluid.

Another object of the present invention is to provide a heating unit, for use by dentists or like mold fabricators, having an electrical heating element which both heats the wax and the instruments used by the dentist to work the wax.

These and other objects, features and advantages of the present invention will become apparent upon reading the following specification, when taken in conjunction with the accompanying drawing.

BRIEF DESCRIPTION OF THE DRAWING

FIG. 1 is a pictorial view of the materials heating apparatus according to a disclosed embodiment of the present invention.

FIG. 2 is a broken away rear pictorial view of the materials heating unit of FIG. 1 with the heating element removed.

FIG. 3 is a broken away rear pictorial view of the materials heating unit of FIG. 1 with the heating element removed, but showing an alternative embodiment thereof.

FIG. 4 is a broken away front pictorial view of a modification of the materials heating unit of FIG. 1 and including finned heat dissipating strip of conductive material for controlling heat dissipation.

DETAILED DESCRIPTION OF THE DISCLOSED EMBODIMENT

Referring now in more detail to the drawings in which like numerals represent like components throughout the several views, FIG. 1 shows the materials heating unit 10 to comprise a heating dish or receptacle 11 which is preferably divided into a number of compartments, such as the three fluid-retaining compartments 13a, 13b, 13c. A bracket 14 is attached to the heating dish 11 by welding or similar means of attachment and protrudes above the upper plane of the heating dish. At the upper end of the bracket 14, the bracket forms a rod holder 15 which comprises an elongated tubular passage 16 through which is inserted a bare metal, rod-shaped heating element 20. The heating element 20 is held firmly in heat conductive relation with the tubular passage 16 of rod holder 15 by a set screw 17 threaded through the rod holder. The heating element 20 is connected by electric cord 21 by way of conventional plug 22 to a source of electric power (not shown), generally at a typical building wall socket. A variable voltage control 23 is preferably provided within the heating element electrical circuit, so as to control the amount of heat output from the heating element 20, and the control 23 can also incorporate an on-off switch to completely remove heating power from the heating element. In operation, wax 28 or similar material which is to be melted is placed in one or more of the compartments 13a, 13b, 13c of the heating dish 11. It is not necessary, for purposes of the invention, that there be more than one compartment 13 in the heating dish 11. The separate compartments can be used for holding wax of different colors or for holding different molten materials. The bare metal heating element 20 is inserted into the passage 16 of the rod holder 15 and screwed tightly in place by set screw 17. A portion 25 of the heating element 20 protrudes from the tubular passage 16 of the rod holder 15 and is exposed to direct contact by free objects such as the wax working instruments 29, thus serving as the instrument heating device 25 of the materials heating apparatus. The heating element is then supplied with electricity, with the amount of heating being controlled by suitable adjustment of the control 23. The bracket 14 and heating dish 11 are both made of a substantially thermoconductive material such as aluminum or the like, so that heat produced by the heating element 20 is conducted through the bracket and through the body of the heating dish to heat and melt the wax 28 retained within the heating dish.

An instrument 29 which is to be used in working with the wax 28 can readily be brought into direct physical contact with the exposed portion until the instrument is sufficiently hot to perform its designated function. It can be seen that once the instrument 29 has been heated by the heating element 20, the instrument need be moved only a short distance to the wax 28. Because there is no open flame, the work piece or mold (not shown) can be positioned relatively near to the heating unit 10.

FIG. 3 shows an alternative embodiment of the heating unit 10 of FIG. 1 which includes an alternative arrangement for attaching the bracket 14 to the heating dish 11. This alternative bracket 14a is removably attached to the dish 11 by a set screw 32 driven through a bracing bar 33 which is fixedly attached to the dish 11. With the set screw 32 loosened, the bracket 14a can be moved vertically up and down through the bracing bar 33 relative to the heating dish 11. In this way, the effective length of the thermally conductive path between the dish 11 and the heating element 20 (not shown in FIG. 3) which is secured in the rod holder can be adjusted in position relative to the heating dish 11. Adjustment of the thermally conductive path provides some variation of the rate at which heat from the heating element 20 is transferred to the dish 11. This adjustable arrangement also gives the user of the heating unit 10 the option to choose from a limited choice of relative positions between the heating element and the dish to accommodate instruments of varying sizes or to provide a convenience for users with shorter or longer fingers and hands.

Another accessory to the materials heating unit 10 of the present invention is the finned strip of conductive material 35 shown in FIG. 4 which is attached to the heating dish 11 at the side 38 of the dish 11 opposite the heating element 20. The finned strip 35, which may be formed to include a number of heat-radiating fins 37, is pivotable about a pin 36 from a first position in which the strip 35 is adjacent to and in parallel alignment with the length of the side 38 of the dish 11, to the position depicted in FIG. 4 in which the strip is aligned perpendicular to the length of the side 28 of the dish. As the strip 35 is pivoted more and more away from its first position it has the effect of increasing the surface area of the receptacle 11. Increasing the surface area increases the heat dissipating area of the receptacle by providing more surface from which the heat can radiate. This finned strip 35 thus provides an adjustable heat control for the heating dish 11 whereby the dish can be variably "cooled down" relative to the heating element 20. In this way, the wax 28 can be heated at a lower rate than the instruments 29 while the heating element is maintained at a uniform heat.

The heating element 20 of the present invention should not be limited to the described design, but rather it can be of any construction and design which serves to heat both the heating dish 11 and provide a second instrument heating portion by which the instruments 29 and the heating dish 11 can be heated from the same heating element and in near proximity to one another.

While this invention has been described in specific detail with particular reference to preferred embodiments thereof, it will be understood that variations and modifications can be effected within the spirit and the scope of the invention as described hereinbefore and as defined in the appended claims.

What is claimed is:

1. A materials heating device comprising:
   a receptacle formed of thermoconductive material;
   heating means mounted in good heat conducting relationship to said receptacle so as to impart heat to said receptacle and to material received therein;
   said heating means being separate from said receptacle and including a portion which is exposed to direct contact by an implement, so that said implement can receive heat from said heating means;
   said heating device further comprising conductive connecting means for connecting said heating element to said receptacle and for conducting heat from said heating element to said receptacle to heat said receptacle;
   said heating means comprising an elongated heating element, and wherein said connecting means comprises a bracket attached to said receptacle and forming an annular holder which surrounds and holds said elongated heating element in good heat transfer relation thereto and in spaced relationship to said receptacle, said annular holder being shorter in length than said elongated heating element whereby a portion of said elongated heating element is exposed beyond said annular holder for easy contact and access by said implement.

2. A materials heating device comprising:
   a heating dish formed of thermoconductive material; and
   a rod shaped heating element heated by electrical current mounted adjacent said heating dish and connected in spaced relationship to said heating dish by a heat conducting bracket means for conducting heat from said heating element to said heating dish to melt materials in said dish, said bracket means including a heating element holder through which said heating element extends, said heating element including an exposed portion protruding from said heating element holder for contacting and heating material not contacting said dish whereby said heating element heats said dish and heats other materials brought into contact with said exposed portion.

3. The device of claim 2 and further comprising means associated with said bracket means for adjustably attaching said bracket means to said dish to selectively position said heating element at varying distances from said receptacle.

4. The device of claim 2 and further comprising a finned strip of thermoconductive material adjustably attached to said dish, selectively adjustable to increase the heat dissipating area of said dish.

* * * * *